US006987170B1

(12) United States Patent
Silverman et al.

(10) Patent No.: US 6,987,170 B1
(45) Date of Patent: Jan. 17, 2006

(54) **CLONING AND EXPRESSION OF RECOMBINANT ADHESIVE PROTEIN MEFP-1 OF THE BLUE MUSSEL, *MYTILUS EDULIS***

(75) Inventors: Heather G. Silverman, Idaho Falls, ID (US); Francisco F. Roberto, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 25 days.

(21) Appl. No.: 10/915,161

(22) Filed: Aug. 9, 2004

(51) Int. Cl.
*C07K 17/00* (2006.01)
*C12P 21/06* (2006.01)

(52) U.S. Cl. ................................. 530/350; 435/69.1
(58) Field of Classification Search .............. 435/69.1; 530/350
See application file for complete search history.

(56) References Cited

U.S. PATENT DOCUMENTS 5,049,504 A * 9/1991 Maugh et al. ......... 435/252.33
5,202,236 A * 4/1993 Maugh et al. ............. 435/69.1
6,465,237 B1 10/2002 Tomlinson

OTHER PUBLICATIONS

Altshul, et al., J. Mol. Biol. 215:403-410 (1990).
Bell, E.C., et al., Mechanical Design of Mussel Byssus: Material Yield Ehances Attachment Strength, *Journal of Experimental Biology*, 199(4): 1005-1017 (1996).
Brown, C.H., Some Structural Proteins of *Mytilus edulis*, *Quarterly Journal of Microscopical Science*, 93(4):487 (1952).
Chivers, R.A., et al., The Strength of Adhesive-Bonded Tissue Joints, *International Journal of Adhesion and Adhesives*, 17(2):127-132 (1997).
Denny, M.W., *Biology and the Mechanics of the Wave Swept Environment*, Princeton: Princeton University Press (1988).
Fulkerson, J.P., et al., Attachment of Epiphyseal Cartilage Cells and 17/28 Rat Osterosarcoma Osteoblasts using Mussel Adhesive Protein. *Journal of Orthopaedic Research*, 8 (6): 793-798 (1990).
Inoue, K., et al., Cloning Sequencing and Sites of Expression of Genes for the Hydroxyarginine-Containing Adhesive-Plaque Protein of the Mussel, *Mytilus galloprovincialis, European Journal of Biochemistry*, 239 (1): 172-176 (1996).
Robin, J.B., et al., Preliminary Evaluation of the Use of Mussel Adhesive Protein in Experimental Epikeratoplasty, Archives of Opthalmology, 106 (7): 973-977 (1988).
Schmidt, S.P., et al., The Combined Effects of Glycyl-L-Histidyl-L-Lysine-Copper (II) and CELL-TAK® (BioPolymers Corp of Farmington, CT) on the Healing of Linear Incision Wounds, Wounds A Compendium of Clinical Research and Practice. 6 (2): 62-67 (1994).
Waite, J.H., J. Comp. Physiol (B), p. 491-496 (1986).
Waite, J.H., The Phylogeny and Chemical Diversity of Quinonetanned Glues and Varnishes, *Comp Biochem Physiol B.*, 97(1): 19-29 (1990).
Waite, J.H., Reverse Engineering of Bioadhesion in Marine Mussels, *Bioartificial Organs II: Technology, Medicine, and Materials Annals of the New York Academy of Sciences*, 875: 301-309 (1999).
Warner, S.C., et al., Expression of Multiple Forms of an Adhesive Plaque Protein in an Individual Mussel, *Mytilus edulis, Marine Biology*, 134 (4): 729-734 (1999).
Weaver, J.K., Isolation, Purification, and Partial Characterization of a Mussel Byssal Precursor Protein, *Mytilus edulis* foot protein 4, MS thesis, University of Delaware, Newark, (1998).
Altschul, et al., Nucleic Acids Res. 25: 3389-3402 (1997).
Burzio, V.A., et al., Mussel Adhesive Enhances the Immobilization of Human Chorionic Gonadotrophin to a Solid Support, *Analytical Biochemistry*, 241 (2): 190-194 (1996).
Crisp, D.J., et al., Adhesion and Substrate Choice in Mussels and Barnacles, *Journal of Colloid and Interface Science*, 104(1): 40-50 (1985).
Inoue, K., et al., The Adhesive Protein cDNA of *Mytilus galloprovincialis* Encodes Decapeptide Repeats but No Hexapeptide Motif, *Biol. Bull*, 186: 349-355 (Jun. 1994).
Inoue, K., et al., Mussel Adhesive Plaque Protein Gene is a Novel Member of Epidermal Growth Factor-like Gene Family, *Journal of Biological Chemistry*, 270 (12): 6698-6701 (1995).
Karlin and Altschul, Proc. Nat'l Acad. Sci. USA 87: 2264-2268 (1990).
Karlin and Altschul, Proc. Nat'l Acad. Sci. USA 90: 5873-5877 (1993).
Miki, D., et al., Expression Sites of Two Byssal Protein Genes of *Mytilus galloprovincialis, Biol. Bull*. 190: 213-217 (Apr. 1996).
Papov, V.V., et al., Hydroxyarginine-Containing Polyphenolic Proteins in the Adhesive Plaques of the Marine Mussel, *Mytilus edulis, Journal of Biological Chemistry*, 270 (34): 20183-20192 (1995).

(Continued)

*Primary Examiner*—Robert A. Wax
*Assistant Examiner*—Agnes Rooke
(74) *Attorney, Agent, or Firm*—Trask Britt P.C.

(57) ABSTRACT

The present invention comprises a *Mytilus edulis* cDNA sequenc having a nucleotide sequence that encodes for the *Mytilus edulis* foot protein-1 (Mefp-1), an example of a mollusk foot protein. Mefp-1 is an integral component of the blue mussels' adhesive protein complex, which allows the mussel to attach to objects underwater. The isolation, purification and sequencing of the Mefp-1 gene will allow researchers to produce Mefp-1 protein using genetic engineering techniques. The discovery of Mefp-1 gene sequence will also allow scientists to better understand how the blue mussel creates its waterproof adhesive protein complex.

14 Claims, 1 Drawing Sheet

OTHER PUBLICATIONS

Qin, X.X., et al., Exotic Collagen Gradients in the Byssus of the Mussel, *Mytilus edulis, Journal of Experimental Biology*, 198(3): 633-644 (1995).

Qin, X.X., et al., A Potential Mediator of Collagenous Block Copolymer Gradients in Mussel Byssal Threads, *Proceedings of the National Academy of Sciences of the United States of America*, 95(18): 10517-10522 (1998).

Rzepecki, L.M., et al., Characerization of Cysteine-rich Polyphenolic Protein Family from the Blue Mussel, *Mytilus edulis*-L, Biological Bulletin, 183 (1): 123-137 (1992).

Saby, C., et al., *Mytilus edulis* Adhesive Protein (MAP) as an Enzyme Immobilization Matrix in the Fabrication of Enzyme-Based Electrodes, *Electroanalysis*, 10 (17): 1193-1199 (1998).

Sever, M.J., et al., Metal-mediated cross-linking in the generation of a marin-mussel adhesive,*Angewandre Chemie* 43(4), 448-450 (no date).

Vreeland, V., et al., Polyphenols and Oxidases in Substratum Adhesion by Marine Algae and Mussels, *Journal of Phycology*, 34 (1): 1-8 (1998).

Waite, J.H., Chem. Ind. P. 607 (1991).

Waite, J.H., Evidence for a Repeating 3,4-Dihydroxyphenylalanine-Containing and Hydroxyproline-Containing Decapeptide in the Adhesive Protein of the Mussel, *Mytilus edulis, Journal of Biological Chemistry*, 258(5): 2911-2915 (1983).

Waite, J.H., et al., Polyphenolic Substance of *Mytilus edulis* Novel Adhesive Containing L-Dopa and Hydroxyproline, *Science*, 212 (4498): 1038-1040 (1981).

Waite, J.H., et al., Polyphosphoprotein from the Adhesive Pads of *Mytilus edulis, Biochemistry*, 40 (9): 2887-2893 (2001).

Yu, M., et al., Role of L-3,4-Dihydroxyphenylalanie in Mussel Adhesive Proteins, *Journal of the American Chemical Society*, 121: 5825-5826 (1999).

* cited by examiner

SEQUENCE LISTING

<160> NUMBER OF SEQ ID NOS: 22

<210> SEQ ID NO 1
<211> LENGTH: 1698
<212> TYPE: DNA
<213> ORGANISM: Mytilus edulis

<400> SEQUENCE: 1

```
atggagggaa tcaaattaaa tctgtgcctc ttgtgtatat ttacctttga cgtcttgggt      60
ttttcaaatg gtaacatata caacgctcat gtctcatctt atgcaggtgc aagcgctggg     120
gcttacaaga aactgcctaa tgcatatcca tacggaacaa agcctgaacc agtatacaaa     180
cctgtgaaga caagttattc ggcaccatat aaaccaccaa cataccaaca actcaaaaag     240
aaagtggact atcgtcctac gaaaagttat ccgccaacat atggatcaaa gacaaactat     300
ctgccacttg caaagaagct gtcatcttac aaacctatta agacaacata taatgcaaag     360
acaaattatc caccagttta taaacctaag atgacttatc ctcctacata caaaccaaag     420
cccagttatc ctccaacata taaatcaaag cccacataca aacctaagat aacatgccct     480
ccaacttata aagcaaagcc cagttatcct ccaacatata aacctaagaa aacttatccc     540
cccacatata aacctaaagt aacctatccc cctacataca aaccaaagcc cagttatcct     600
ccaatatata aatcaaagcc cacatacaaa cctaagataa catccctcc aacatataaa      660 gcaaagccaa gttatcctcc aacttataaa gcaaaaccaa gttatcctcc aacttataaa     720
gcaaagccaa cttataaagc aaagccaact tatccttcaa cgtataaagc aaagccaact     780
tatcctccaa cttataaagc aaaaccaagt tatcctccaa cttataaagc aaaaccaagt     840
tatcctccaa cttataaagc aaagccaact tatatagcaa agccaagtta tcctccaact     900
tataaagcaa aaccaagtta tcctccaact tataaagcaa agccaagtta tcctccaact     960
tataaagcaa aatcaagtta tcctccaact tataaagcaa aaccaactta taaagcaaag    1020
ccaacttatc cttcaacgta taaagcaaaa ccaagttatc ctccaactta taaagcaaaa    1080
ccaacttata aagcaaagcc aacttatcct tcaacttata aagcaaaacc aacttatcct    1140
tcaacgtata aagcaaaacc aagttatcct ccaacttata aacctaaaat aagttatcct    1200
ccaacttata aagcaaaacc aagttatcct tcaacttata aagcaaaatc aagttatcct    1260
ccaacttata aagcaaaacc aagttatcct ccaacttata aagcaaagcc aacttataaa    1320
gcaaagccaa cttatccttc aacgtataaa gcaaagccaa cttataaagc aaagccaact    1380
tatcctccaa cttataaagc aaaaccaagt tatcctccaa catataaacc aaagccaagt    1440
tatcctccaa cttataaatc caagtcaagt tatccctctt cctacaaacc taagaaaact    1500
tatcccccca cctataaacc taaactaacc tatcctccaa catataaacc aaagccaagt    1560
tatccaccat cttataaacc taagattact tatccctcaa cttataaatt gaagccaagt    1620
```

```
tatcctccaa catacaaatc taaaacaagt taccctccta catataacaa aaagatcagc    1680
tatccatcac aatattaa                                                  1698
```

<210> SEQ ID NO 2
<211> LENGTH: 565
<212> TYPE: PRT
<213> ORGANISM: Mytilus edulis

<400> SEQUENCE: 2

```
Met Glu Gly Ile Lys Leu Asn Leu Cys Leu Leu Cys Ile Phe Thr Phe
1               5                   10                  15

Asp Val Leu Gly Phe Ser Asn Gly Asn Ile Tyr Asn Ala His Val Ser
            20                  25                  30

Ser Tyr Ala Gly Ala Ser Ala Gly Ala Tyr Lys Lys Leu Pro Asn Ala
        35                  40                  45

Tyr Pro Tyr Gly Thr Lys Pro Glu Pro Val Tyr Lys Pro Val Lys Thr
    50                  55                  60

Ser Tyr Ser Ala Pro Tyr Lys Pro Pro Thr Tyr Gln Gln Leu Lys Lys
65                  70                  75                  80

Lys Val Asp Tyr Arg Pro Thr Lys Ser Tyr Pro Pro Thr Tyr Gly Ser
                85                  90                  95

Lys Thr Asn Tyr Leu Pro Leu Ala Lys Lys Leu Ser Ser Tyr Lys Pro
            100                 105                 110

Ile Lys Thr Thr Tyr Asn Ala Lys Thr Asn Tyr Pro Pro Val Tyr Lys
        115                 120                 125

Pro Lys Met Thr Tyr Pro Pro Thr Tyr Lys Pro Lys Pro Ser Tyr Pro
    130                 135                 140

Pro Thr Tyr Lys Ser Lys Pro Thr Tyr Lys Pro Lys Ile Thr Cys Pro
145                 150                 155                 160

Pro Thr Tyr Lys Ala Lys Pro Ser Tyr Pro Pro Thr Tyr Lys Pro Lys
                165                 170                 175

Lys Thr Tyr Pro Pro Thr Tyr Lys Pro Lys Val Thr Tyr Pro Pro Thr
            180                 185                 190

Tyr Lys Pro Lys Pro Ser Tyr Pro Pro Ile Tyr Lys Ser Lys Pro Thr
        195                 200                 205

Tyr Lys Pro Lys Ile Thr Tyr Pro Pro Thr Tyr Lys Ala Lys Pro Ser
    210                 215                 220

Tyr Pro Pro Thr Tyr Lys Ala Lys Pro Ser Tyr Pro Pro Thr Tyr Lys
225                 230                 235                 240

Ala Lys Pro Thr Tyr Lys Ala Lys Pro Thr Tyr Pro Ser Thr Tyr Lys
                245                 250                 255

Ala Lys Pro Thr Tyr Pro Pro Thr Tyr Lys Ala Lys Pro Ser Tyr Pro
            260                 265                 270

Pro Thr Tyr Lys Ala Lys Pro Ser Tyr Pro Pro Thr Tyr Lys Ala Lys
        275                 280                 285

Pro Thr Tyr Ile Ala Lys Pro Ser Tyr Pro Pro Thr Tyr Lys Ala Lys
    290                 295                 300

Pro Ser Tyr Pro Pro Thr Tyr Lys Ala Lys Pro Ser Tyr Pro Pro Thr
305                 310                 315                 320

Tyr Lys Ala Lys Ser Ser Tyr Pro Pro Thr Tyr Lys Ala Lys Pro Thr
                325                 330                 335

Tyr Lys Ala Lys Pro Thr Tyr Pro Ser Thr Tyr Lys Ala Lys Pro Ser
            340                 345                 350
```

-continued

```
Tyr Pro Pro Thr Tyr Lys Ala Lys Pro Thr Tyr Lys Ala Lys Pro Thr
        355                 360                 365

Tyr Pro Ser Thr Tyr Lys Ala Lys Pro Thr Tyr Pro Ser Thr Tyr Lys
        370                 375                 380

Ala Lys Pro Ser Tyr Pro Pro Thr Tyr Lys Pro Lys Ile Ser Tyr Pro
385                 390                 395                 400

Pro Thr Tyr Lys Ala Lys Pro Ser Tyr Pro Ser Thr Tyr Lys Ala Lys
            405                 410                 415

Ser Ser Tyr Pro Pro Thr Tyr Lys Ala Lys Pro Ser Tyr Pro Pro Thr
            420                 425                 430

Tyr Lys Ala Lys Pro Thr Tyr Lys Ala Lys Pro Thr Tyr Pro Ser Thr
        435                 440                 445

Tyr Lys Ala Lys Pro Thr Tyr Lys Ala Lys Pro Thr Tyr Pro Pro Thr
        450                 455                 460

Tyr Lys Ala Lys Pro Ser Tyr Pro Pro Thr Tyr Lys Pro Lys Pro Ser
465                 470                 475                 480

Tyr Pro Pro Thr Tyr Lys Ser Lys Ser Ser Tyr Pro Ser Ser Tyr Lys
            485                 490                 495

Pro Lys Lys Thr Tyr Pro Pro Thr Tyr Lys Pro Lys Leu Thr Tyr Pro
            500                 505                 510

Pro Thr Tyr Lys Pro Lys Pro Ser Tyr Pro Ser Tyr Lys Pro Lys
            515                 520                 525

Ile Thr Tyr Pro Ser Thr Tyr Lys Leu Lys Pro Ser Tyr Pro Pro Thr
        530                 535                 540

Tyr Lys Ser Lys Thr Ser Tyr Pro Pro Thr Tyr Asn Lys Lys Ile Ser
545                 550                 555                 560

Tyr Pro Ser Gln Tyr
            565
```

<210> SEQ ID NO 3
<211> LENGTH: 23
<212> TYPE: DNA
<213> ORGANISM: Artificial
<220> FEATURE:
<223> OTHER INFORMATION: Mefp-1 RT-PCR Primer forward-516

<400> SEQUENCE: 3
gagctcgcat catggaggga atc          23

<210> SEQ ID NO 4
<211> LENGTH: 31
<212> TYPE: DNA
<213> ORGANISM: Artificial
<220> FEATURE:
<223> OTHER INFORMATION: Mefp-1 RT-PCR Primer reverse-517

<400> SEQUENCE: 4
gcggccgcca cttaatattg tgatggatag c          31

<210> SEQ ID NO 5
<211> LENGTH: 20
<212> TYPE: DNA
<213> ORGANISM: Artificial
<220> FEATURE:
<223> OTHER INFORMATION: T7 primer

<400> SEQUENCE: 5
taatacgact cactataggg          20

```
<210> SEQ ID NO 6
<211> LENGTH: 21
<212> TYPE: DNA
<213> ORGANISM: Artificial
<220> FEATURE:
<223> OTHER INFORMATION: V5C term reverse primer

<400> SEQUENCE: 6
accgaggaga gggttaggga t                                             21

<210> SEQ ID NO 7
<211> LENGTH: 18
<212> TYPE: DNA
<213> ORGANISM: Artificial
<220> FEATURE:
<223> OTHER INFORMATION: Sequencing Primer HS506

<400> SEQUENCE: 7
tttcggttag agcggatg                                                 18

<210> SEQ ID NO 8
<211> LENGTH: 20
<212> TYPE: DNA
<213> ORGANISM: Artificial
<220> FEATURE:
<223> OTHER INFORMATION: Sequencing Primer HS 507

<400> SEQUENCE: 8
agggcgtgaa tgtaagcgtg                                               20

<210> SEQ ID NO 9
<211> LENGTH: 19
<212> TYPE: DNA
<213> ORGANISM: Artificial
<220> FEATURE:
<223> OTHER INFORMATION: F#21Int859 by HS

<400> SEQUENCE: 9
gcaaagccaa cttatatag                                                19

<210> SEQ ID NO 10
<211> LENGTH: 22
<212> TYPE: DNA
<213> ORGANISM: Artificial
<220> FEATURE:
<223> OTHER INFORMATION: R#21Int529 by HS

<400> SEQUENCE: 10
gaagagggat aacttgactt gg                                            22

<210> SEQ ID NO 11
<211> LENGTH: 21
<212> TYPE: DNA
<213> ORGANISM: Artificial
<220> FEATURE:
<223> OTHER INFORMATION: FP-1 EpiCentre

<400> SEQUENCE: 11
cccaatacgc aaaccgcctc t                                             21

<210> SEQ ID NO 12
<211> LENGTH: 25
<212> TYPE: DNA
<213> ORGANISM: Artificial
<220> FEATURE:
<223> OTHER INFORMATION: RP-1 EpiCentre
```

-continued

```
<400> SEQUENCE: 12
ttagaaaaat aaacaaatag gggtt                                           25

<210> SEQ ID NO 13
<211> LENGTH: 2502
<212> TYPE: DNA
<213> ORGANISM: Mytilus galloprovincialis

<400> SEQUENCE: 13
ctgcatcatg gagggaatca aattaaatct gtgcctcttg tgtatattta cctgtgacat     60
cttgggtttt tcaaatggta acatatacaa cgctcatggt tcagcttatg caggtgcaag    120
tgctggggct tacaagacac tgcctaatgc atatccatac ggaacaaagc atggaccagt    180
atacaaacct gtgaagacaa gttatcatcc tacgaatagt tatccgccaa catatggatc    240
aaagacaaac tatctgccac ttgcaaagaa gctgtcatct acaaaccta ttaagacaac     300 atataatgca agacaaatt atccaccagt ttataaacct aagatgactt atcctccaac     360
ttataaacct aagcccagtt atcctccaac atataaacca agccaagtt atccagcaac     420 ttataaatcc aagtcaagtt atccctcttc atacaaacct aagaaaactt atcctccaac    480
atataaacct aaactaacct atcctccaac atataaacca aaccaagtt atcctccaac     540 atataaacca agccaagtt atccagcaac ttataaatcc aagtcaagtt atcccccttc     600
atataaaact aagaaaactt atccctcttc atataaacct aagaaaactt atccttcaac    660
gtataaacca aaagtgagtt atcccccaac atacaaatca aaaagtctt atcctccaat     720 atataagaca aaggcaagtt atccatcatc atataaacct aaaaaaacgt atccttcaac    780
ttataaaccc aagataagtt atccaccaac gtataaagca aagcccagtt atccaacatc    840
ttatagagca aaaccaagct atccttcaac ttataaggca aaaccaagtt atcctccaac    900
ttataaagca aaaccaagtt atcctccaac ttataaagca aagccaactt atccttcaac    960
gtataaagca aaaccaagct atcctccaac ttataaagca aaaccaagct atcctccaac   1020
gtataaagca aaaccgagtt atccaccatc atataaacct aaaacaactt atcctccaag   1080
ttataaacct aagataagtt atcctccaac ttataaggca aaaccaagtt atcctccaat   1140
ttataaagca aaaccaagtt atcctccaac ttataaagca aaaccaagtt atcttccaac   1200
ttataaagca aaaccaagtt atcccccaac gtataaagca aaaccgagat atcctacaac   1260
ttataaagca aaaccaagtt atcctccaac ttataaagca aaaccaagtt atcctccaac   1320
gtataaagca aaactaagtt atcctccaac gtataaagca aaaccgagtt atcctccaac   1380
ttataaagca aaaccaagtt atcctccaac ttataaagca aaaccaagtt atcctccaac   1440 tttataaaaca aagccaagtt atcctcgaac gtataaagca aaaccaagtt attcttcaac   1500
ttataaagca aaaccaagtt atcctccaac ttataaagca aaaccaagtt atcctccaac   1560
gtataaagca aagccaagtt atcctccaac ttataaagca aaaccaagtt atcctccaac   1620
atataaagca aaaccaagtt atcccccaac ttataaagca aaaccaagtt atcctcaaac   1680
ttataaagca aaatcaagtt atcctccaac ttataaagca aagccaagtt atcctccaac   1740
ttataaagca aaaccaagtt atcctccaac ttataaagca aagccaagtt atcctccaac   1800
ttataaagca aaaccaagtt atcctccaac ttataaagca aagccaagtt atcctccaac   1860
ttataaagca aaaccaagtt atcctccaac ttataaagca aaaccaagtt atcctccaac   1920
ttataaagca aaaccaagtt atcctccaac ttataaagca aagccaagtt atccagcaac   1980
ttatccttca acgtataaag caaagccaag ttatcctcca acttataaag caaaaccaag   2040
```

```
ttatcctcca acatataaac caaagccaag ttatccacca acatataaat ccaagtcaag    2100
ttatccctct tcatacaaac ctaagaaaac ttatcccccc acatataaac ctaaactaac    2160
ctatccccca atatataaac caaagccaag ttatcctcca acatacaaat ctagttaccc    2220
tcctagatat aaaaaaaaga tcagctatcc atcacaatat taagtgaaga caagttatcc    2280
ccaagcatat gaaccaacaa acagctatta atctcaatat taaaagtatt aattaaaata    2340
ttcatattac tgtactacac attttaacgt ttgtgttgat gaggaacaga tgaacatttg    2400
aaagtaatac ataatcgggg ttaatgattt gttatattca atctttatgt ttgtgattgg    2460
ttatgttctt gaaatattgt ttaaaataaa tgtttatttt tt                      2502

<210> SEQ ID NO 14
<211> LENGTH: 4
<212> TYPE: PRT
<213> ORGANISM: Artificial
<220> FEATURE:
<223> OTHER INFORMATION: Amino Acid Sequence for Mefp-1 PCR Primer 516
      (f)

<400> SEQUENCE: 14

Met Glu Gly Ile
1

<210> SEQ ID NO 15
<211> LENGTH: 5
<212> TYPE: PRT
<213> ORGANISM: Artificial
<220> FEATURE:
<223> OTHER INFORMATION: Protein sequence for Mefp-1 PCR Primer 517 (r)

<400> SEQUENCE: 15

Tyr Pro Ser Gln Tyr
1               5

<210> SEQ ID NO 16
<211> LENGTH: 378
<212> TYPE: DNA
<213> ORGANISM: Mytilus edulis

<400> SEQUENCE: 16
tcaacttata aagcaaagcc aacttatcct ccaacttata aagcaaaacc aagttatcct     60
ccaacatatg aaccaaagcc aagttatcct ccaacttata aatccaagtc aagttatccc    120
tcttcataca aacctaagaa aacttatccc cccacatata aacctaaact aacatatcct    180
ccaacatata aaccaaagcc aagttatcca gcatcttata aacctaagat tacttatcca    240
ttgaagccaa gttatcctcc aacatacaaa tctaaaacaa gttaccctcc tacatataac    300
aaaaagatca gctatccatc atcatataaa gctaagacaa gttatccccc agcatataaa    360
ccaacaaaca gatattaa                                                  378

<210> SEQ ID NO 17
<211> LENGTH: 12
<212> TYPE: DNA
<213> ORGANISM: Artificial
<220> FEATURE:
<223> OTHER INFORMATION: Partial sequence of Mgfp-1 (f)

<400> SEQUENCE: 17
atggagggaa tc                                                         12
```

<210> SEQ ID NO 18
<211> LENGTH: 31
<212> TYPE: DNA
<213> ORGANISM: Artificial
<220> FEATURE:
<223> OTHER INFORMATION: Mgfp-1 partial sequence (r)

<400> SEQUENCE: 18
gctatccatc acaatattaa gtgaagacaa g          31

<210> SEQ ID NO 19
<211> LENGTH: 31
<212> TYPE: DNA
<213> ORGANISM: Artificial
<220> FEATURE:
<223> OTHER INFORMATION: Primer 517 compliment

<400> SEQUENCE: 19
gctatccatc acaatattaa gtggcggccg c          31

<210> SEQ ID NO 20
<211> LENGTH: 120
<212> TYPE: PRT
<213> ORGANISM: Mytilus edulis

<400> SEQUENCE: 20

Ser Thr Tyr Lys Ala Lys Pro Thr Tyr Pro Thr Tyr Lys Ala Lys
1               5                   10                  15

Pro Ser Tyr Pro Pro Thr Tyr Glu Pro Lys Pro Ser Tyr Pro Pro Thr
            20                  25                  30

Tyr Lys Ser Lys Ser Ser Tyr Pro Ser Ser Tyr Lys Pro Lys Thr
        35                  40                  45

Tyr Pro Pro Thr Tyr Lys Pro Lys Leu Thr Tyr Pro Pro Thr Tyr Lys
    50                  55                  60

Pro Lys Pro Ser Tyr Pro Ala Ser Tyr Lys Pro Lys Ile Thr Tyr Pro
65                  70                  75                  80

Leu Lys Pro Ser Tyr Pro Pro Thr Tyr Lys Ser Lys Thr Ser Tyr Pro
                85                  90                  95

Pro Thr Tyr Asn Lys Lys Ile Ser Tyr Pro Ser Ser Tyr Lys Ala Lys
            100                 105                 110

Thr Ser Tyr Pro Pro Ala Tyr Lys
        115                 120

<210> SEQ ID NO 21
<211> LENGTH: 6
<212> TYPE: PRT
<213> ORGANISM: Mytilus edulis

<400> SEQUENCE: 21

Ala Lys Pro Thr Tyr Lys
1               5

<210> SEQ ID NO 22
<211> LENGTH: 10
<212> TYPE: PRT
<213> ORGANISM: Mytilus edulis
<220> FEATURE:
<221> NAME/KEY: MOD_RES
<222> LOCATION: (3)..(3)
<223> OTHER INFORMATION: P of residue 3 is trans-4-hydroxy-L-proline
<220> FEATURE:
<221> NAME/KEY: MOD_RES
<222> LOCATION: (5)..(5)
<223> OTHER INFORMATION: Y of residue 5 is 3, 4-dihydroxyphenyl-alanine

```
-continued

<220> FEATURE:
<221> NAME/KEY: MOD_RES
<222> LOCATION: (6)..(6)
<223> OTHER INFORMATION: P of residue 6 is trans-2,3-cis-3,4-
      dihydroxyproline
<220> FEATURE:
<221> NAME/KEY: MOD_RES
<222> LOCATION: (7)..(7)
<223> OTHER INFORMATION: P of residue 7 is rans-4-hydroxy-L-proline
<220> FEATURE:
<221> NAME/KEY: MOD_RES
<222> LOCATION: (9)..(9)
<223> OTHER INFORMATION: Y of residue 9 is 3, 4-dihydroxyphenyl-alanine

<400> SEQUENCE: 22

Ala Lys Pro Ser Tyr Pro Pro Thr Tyr Lys
1               5                   10
```

US 6,987,170 B1

CLONING AND EXPRESSION OF RECOMBINANT ADHESIVE PROTEIN MEFP-1 OF THE BLUE MUSSEL, *MYTILUS EDULIS*

U.S. GOVERNMENT RIGHTS

The United States Government has certain rights in this invention pursuant to Contract No. DE-AC07-99JD13727, and Contract No. AC07-05JD14517 between the United States Department of Energy and Battelle Energy Alliance, LLC.

CROSS REFERENCED APPLICATIONS

This patent application was filed by Applicants on the same day as another patent application filed by Applicants entitled "CLONING AND EXPRESSION OF RECOMBINANT ADHESIVE PROTEIN MEFP-2 OF THE BLUE MUSSEL, *MYTILUS EDULIS*," having Ser. No. 10/915,160 filed Aug. 9, 2004.

TECHNICAL FIELD

The invention relates to isolated or purified nucleic acid molecules encoding an adhesive protein, for example, Mefp-1 of the blue mussel, *Mytilus edulis*. Adhesives that can be derived from the present invention can be used in a variety of fields including but not limited to: military applications, construction products, plastics, electronics, automobile and aviation products as well as several biomedical fields.

SEQUENCE LISTINGS

The electronic readable copy and paper copy of the sequence listings for this invention are identical.

BACKGROUND OF THE INVENTION

*Mytilus edulis*, also termed the common edible mussel or blue mussel, constitutes most of the world's commercial production of cultured mussels, along with the closely related species *Mytilus galloprovincialis*. Besides their use in food culturing, mussels (which is an example of a molusk) have also been used to monitor pollutants in coastal marine waters. The most extensive research about the adhesive properties of mussels has been with *M. edulis*.

Marine mussels, like the edible blue mussel, *M. edulis*, attach to a variety of surfaces in an aqueous environment using a natural adhesive that is incredibly strong and durable. There are no conventional glues that can be applied in an aqueous environment and are impervious to water and turbulent forces. Prior research has shown that one of the proteins in the adhesive, *Mytilus edulis* foot protein 1 (Mefp-1), bonds to glass, plastic, wood, concrete and Teflon. Nine other adhesive-related proteins from *M. edulis* have been identified to date. A tenth is implicated, but has not been identified. The precise mechanism for assembly of the ten proteins is not understood (Mefp-1, -2, -3, -4, -5; Collagens: Precollagen-D, -P (variant P22 and P33), Precollagen-NG, Proximal Matrix Thread Protein (1 and 1a); catechol oxidase). There also may be additional proteins involved in the formation of the adhesive.

Individual protein components have been previously identified from byssal structures through protein isolation and amino acid analysis, revealing repetitive amino acid motifs and modified amino acids with unique characteristics not found in other biological systems. Proposed mechanisms for the strength and waterproof properties of the adhesive formed relate to these recurring amino acid motifs and hydroxylated amino acids found in many of the protein components. Commercial recombinant protein products consisting of either the partial amino acid sequence of Mefp-1 or repeats of the unique decapeptide motif have been marketed in the past. However, no commercial product incorporates any of the other proteins known to be involved in underwater adhesion by the *M. edulis* mussel. Furthermore, these products are a result of protein isolation techniques and NOT recombinant DNA techniques.

Initial strategies for identifying the adhesive proteins of the byssus of *M. edulis* involved purification of the proteins directly from the byssi of thousands of animals. About 10,000 mussels are needed to produce 1 gram of adhesive. Thus, subsequent purification and microscopic analysis require(d) the sacrifice of many mussels. This is neither environmentally friendly nor economically practical. When the original mussel adhesive protein, MAP, was identified, only the amino acid motif common to this protein, also referred to as Mefp-1, (a decapeptide repeat occurring ~80 times) was used in an alternate host production scheme. MAP recombinant protein did/does have substantial adhesive properties; however, the (complete) gene sequence for Mefp-1 and the other proteins involved in byssus formation are necessary for mimicking the bioadhesive. Therefore, isolating, purifying and sequencing the DNA sequence of *M. edulis*' foot protein-1 (Mefp-1) are critically important and are objectives of the present invention.

Figure 1:
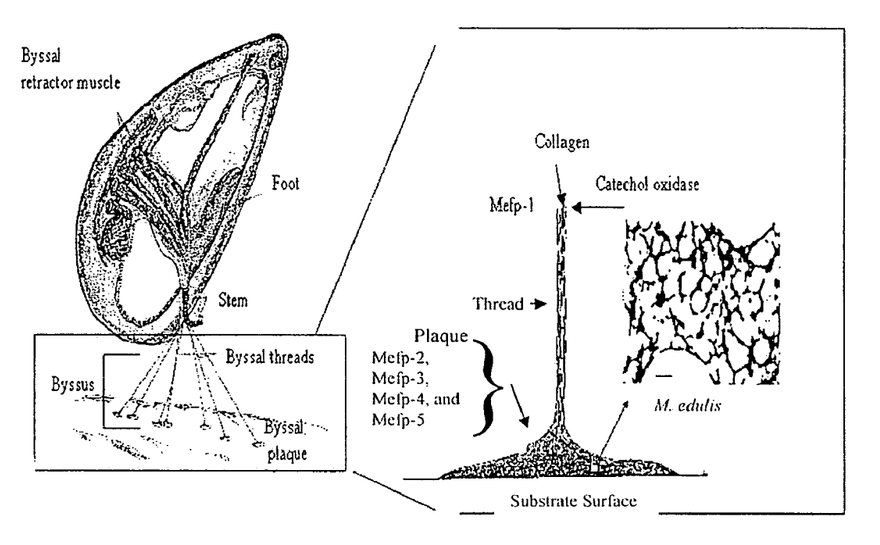

The mussel byssus is an extracorporeal structure that consists of a stem, thread, and a plaque (also referred to as a pad or disc) (See FIG. 1) This exogenous attachment device was first described in Brown C H, Some Structural Proteins of *Mytilus edulis*, *Quarterly Journal of Microscopical Science*, 93(4): 487 (1952). High concentrations of polyphenolic proteins (e.g. L-DOPA), the presence of collagen, and the presence of a catechol oxidase were among the first observations of byssal attachments. Environmental factors such as salinity, temperature, pH, season, and substratum choice, as well as biological factors such as age and metabolic state of the animal effect the efficiency and strength of bonding/attachment. See Crisp D J, Walker G, Young G A, Yule A B, Adhesion and Substrate Choice in Mussels and Barnacles, *Journal of Colloid and Interface Science*, 104 (1): 40–50 (1985).

The stem is rooted in the byssal retractor muscles at the base of the foot organ. See Crisp D J, Walker G, Young G A, Yule A B, Adhesion and Substrate Choice in Mussels and Barnacles, *Journal of Colloid and Interface Science*, 104 (1): 40–50 (1985). The byssal threads, flexible structures of variable dimensions (e.g. ~0.1 mm diameter, 2–4 cm length) and strength, originate from the stem. A byssal thread consists of a flexible, collagenous inner core surrounded by a hard, browned polyphenolic protein. Numerous researchers photographed the collagen core in the 1930's (See Brown C H, Some Structural Proteins of *Mytilus edulis*, *Quarterly Journal of Microscopical Science*, 93(4): 487 (1952))—well before three unique, collagenous proteins were identified and characterized by J. H. Waite and colleagues. The outer polyphenolic protein, believed to undergo a curing or quinone tanning-type reaction with a specialized catechol/polyphenol oxidase enzyme, is traditionally designated as *Mytilus edulis* foot protein 1, Mefp-1, or MAP. (Designation of the byssal thread polyphenolic adhesive protein, as well as subsequent adhesive proteins identified in

*M. edulis*, is preceded by the genus and species: e.g. *Mytilus edulis* foot protein 1=Mefp-1).

The breaking energy of byssal threads is reported to be $12.50 \times 10^6$ Jm$^{-3}$, vs tendon ($2 \times 10^6$ Jm$^{-3}$ to $5 \times 10^6$ Jm3) and silk ($50 \times 10^6$ Jm$^{-3}$ to $180 \times 10^6$ Jm$^{-3}$; See Denny M W, *Biology and the Mechanics of the Wave Swept Environment*, Princeton: Princeton University Press (1988); Qin X X, Waite J H, Exotic Collagen Gradients in the Byssus of the Mussel, *Mytilus edulis, Journal of Experimental Biology*, 198 (3): 633–644 (1995). Bond strengths range from 0.1 to $10 \times 10^6$ Nm$^{-2}$ depending on the substratum. (See Waite J H, Reverse Engineering of Bioadhesion in Marine Mussels, *Bioartificial Organs II: Technology, Medicine, and Materials Annals of the New York Academy of Sciences*, 875: 301–309 (1999). Byssal thread strength at the distal portion of threads is as strong as vertebrate tendon, but 3–5× more extensible (See Qin X X, Waite J H, A Potential Mediator of Collagenous Block Copolymer Gradients in Mussel Byssal Threads, *Proceedings of the National Academy of Sciences of the United States of America*, 95 (18): 10517–10522 (1998). Byssal thread strength at the proximal portion of threads is weaker, but 15–20× more extensible. Strain energy density of threads approaches that of silk at approximately 6× tougher than tendon. Byssal threads can recover initial length and stiffness given sufficient relaxation time (See Bell E C, Gosline J M, Mechanical Design of Mussel Byssus: Material Yield Enhances Attachment Strength, *Journal of Experimental Biology*, 199 (4): 1005–1017 (1996). The byssal structure culminates in a polyphasic plaque of varying size, dependent upon both the size of the animal and the age of the byssus (See Crisp D J, Walker G, Young G A, Yule A B, Adhesion and Substrate Choice in Mussels and Barnacles, *Journal of Colloid and Interface Science*, 104 (1): 40–50 (1985). Plaques are commonly only ~0.15 mm in diameter where they meet the thread, and ~2–3 mm diameter at the substrate interface. Plaque formation occurs from the deposition of proteins that originate from the foot organ. To date, four specialized adhesive proteins have been identified in byssal plaques from *M. edulis*: Mefp-2, Mefp-3, Mefp-4 and Mefp-5.

In spite of the extensive research in this area, and relative success in patenting and commercializing aspects of these adhesive proteins, a complete understanding of how the byssus is assembled from its component proteins, and the role each protein plays in successful assembly and attachment has not been achieved. A major hurdle has been, and remains, large-scale production of the protein in quantities that allow extensive study outside of the byssus. This invention describes the nucleotide sequence from a cDNA for Mefp-1 for the first time.

SUMMARY OF THE INVENTION

One aspect of the invention is an isolated and purified nucleic acid comprising the nucleotide sequence in clone #21 (SEQ ID. NO: 1; a c-DNA sequence) which encodes a biologically active Mefp-1 peptide fragment.

Another aspect of the invention is an isolated and purified nucleic acid comprising the nucleotide sequence in LIV E7 (SEQ ID NO: 16) which encodes an Mefp-1 peptide fragment.

The invention also relates to methods of using the isolated and purified DNA sequences to express the polypeptides which they encode.

Yet another aspect of the invention is a method of producing Mefp-1 which comprises incorporating the nucleic acid having the sequence in (SEQ ID NO: 1) into an expression vector, transforming a host cell with the vector and culturing the transformed host cell under conditions which result in expression of the gene.

Another aspect of the invention is a nucleic acid sequence that is capable of hybridizing under stringent conditions to a nucleotide sequence found in (SEQ ID NO: 1), or its complement.

Another aspect of the invention is a nucleic acid molecule that includes the nucleotide sequence set forth in (SEQ ID NO: 1) or a degenerate variant thereof.

Another aspect of the invention is an RNA molecule that includes the nucleotide sequence set forth in (SEQ ID NO: 1) or degenerate variants thereof, wherein Uracil (U) is substituted for Thymine (T).

Also included in the invention are nucleotides carrying modifications such as substitutions, small deletions, insertions or inversions which still encode proteins having substantially the same activity as the proteins of (SEQ ID NO: 2) or (SEQ ID NO: 20). Included are nucleic acid molecules having a sequence which is at least 90% identical to the nucleotide sequence shown in (SEQ ID NO: 1).

Another aspect of this invention is genetically engineered polypeptides created using the isolated and purified nucleotide sequences of this invention.

Yet another aspect of this invention is utilizing the genetically engineered polypeptides created using the isolated and purified nucleotide sequences of this invention.

BRIEF DESCRIPTION OF THE DRAWINGS

The only drawing is a schematic illustration of the byssal structures of *M. edulis* adapted from Waite J. H., Chem. Ind. p. 607 (1991) and Waite J. H, J. Comp. Physiol (B), p. 451 (1986).

DETAILED DESCRIPTION OF THE PREFERRED EMBODIMENTS

In practicing the present invention several conventional techniques in microbiology and molecular biology (recombinant DNA) are used. Such techniques are well known and are explained in, for example, Sambrook, 1999, Molecular Cloning: A Laboratory Manual, Second Edition, Cold Spring Harbor Laboratory Press, Cold Spring Harbor, N.Y.; DNA Cloning: A practical Approach, 1985 (D. N. Glover ed); Current Protocols in Molecular Biology, John Wiley & Sons, Inc. (1994) and all more recent editions of these publications.

Definitions

Before proceeding further with a description of the specific embodiments of the present invention, a number of terms will be defined.

As used herein, a compound or molecule is an organic or inorganic assembly of atoms of any size, and can include macromolecules, peptides, polypeptides, whole proteins, and polynucleotides.

As used herein, a polynucleotide is a nucleic acid of more than one nucleotide. A polynucleotide can be made up of multiple poly-nucleotide units that are referred to be a description of the unit. For example, a polynucleotide can comprise within its bounds a polynucleotide(s) having a coding sequence(s), a polynucleotide(s) that is a regulatory region(s) and/or other polynucleotide units commonly used in the art.

The isolated nucleic acid molecule of the present invention can include a deoxyribonucleic acid molecule (DNA), such as genomic DNA and complementary cDNA which can be single (coding or noncoding strand) or double stranded, as well as synthetic DNA, such as synthesized single stranded polynucleotide. The isolated nucleic acid molecule of the present invention can also include a ribonucleic acid molecule (RNA).

The determination of percent identity or homology between two sequences is accomplished using the algorithm of Karlin and Altschul (1990) Proc. Nat'l Acad. Sci. USA 87: 2264–2268, modified as in Karlin and Altschul (1993) Proc. Nat'l Acad. Sci. USA 90:5873–5877. Such an algorithm is incorporated into the NBLAST and XBLAST programs of Altschul et al. (1990) J. Mol. Biol. 215:403–410. BLAST nucleotide searches are performed with the NBLAST program, score=100, wordlength=12 to obtain nucleotide sequences homologous to the nucleic acid molecules of the invention. BLAST protein searches are performed with the XBLAST program, score=50, wordlength=3 to obtain amino acid sequences homologous to the protein molecules of the invention. To obtain gapped alignments for comparison purposes, Gapped BLAST is utilized as described in Altschul et al. (1997) Nucleic Acids Res. 25: 3389–3402. When utilizing BLAST and Gapped BLAST programs, the default parameters of the respective programs (e.g., XBLAST and NBLAST) are used. See the website for the National Center for Biological Information.

As used herein, the terms hybridization (hybridizing) and specificity (specific for) in the context of nucleotide sequences are used interchangeably. The ability of two nucleotide sequences to hybridize to each other is based upon a degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the conditions of stringency which include: temperature, solvent ratios, salt concentrations, and the like.

In particular, selective hybridization pertains to conditions in which the degree of hybridization of a polynucleotide of the invention to its target would require complete or nearly complete complementarity. The complementarity must be sufficiently high as to assure that the polynucleotide of the invention will bind specifically to the target relative to binding other nucleic acids present in the hybridization medium. With selective hybridization, complementarity will be 90–100%, preferably 95–100%, more preferably 100%.

The term stringent conditions is known in the art from standard protocols (e.g. Current Protocols in Molecular Biology, editors F. Ausubel et al., John Wiley and Sons, Inc. 1994) and is when hybridization to a filter-bound DNA in 0.5M $NaHPO_4$ (pH7.2), 7% sodium dodecyl sulfate (SDS), 1 mM EDTA at +65° C., and washing in 0.1×SSC/0.1% SDS at +68° C. is performed.

Degenerate variant is the redundancy or degeneracy of the genetic code as is well known in the art. Thus the nucleic acid sequences shown in the sequence listing provided only examples within a larger group of nucleic acids sequences that encode for the polypeptide desired.

Isolated nucleic acid will be nucleic acid that is identified and separated from contaminant nucleic acid encoding other polypeptides from the source of nucleic acid. The nucleic acid may be labeled for diagnostic and probe purposes, using any label known and described in the art as useful in connection with diagnostic assays. For example, a suitable nucleotide sequence could contain at least 500 nucleotides.

Because the genetic code is degenerate, more than one codon may be used to encode a particular amino acid, and therefore, the amino acid sequence can be encoded by any set of similar DNA oligonucleotides. With respect to nucleotides, therefore, the term derivative(s) is also intended to encompass those DNA sequences that contain alternative codons which code for the eventual translation of the identical amino acid.

Mussel adhesive proteins are scleroproteins—proteins contributing mechanical strength to supporting structures in animals. Familiar scleroproteins include collagen, silk, elastin, fibroin, keratin, fibrin and resilin. Quinone tanning requires a catecholic precursor (such as catechol oxidase) and the presence of tanned scleroproteins. See, Waite J H, The Phylogeny and Chemical Diversity of Quinone-tanned Glues and Varnishes, *Comp Biochem Physiol B.*, 97(1): 19–29 (1990). Individual adhesive proteins from mussels are derived from the foot organ of the animals. The proteins are stockpiled in the foot, and then secreted or released into the environment to form strong attachments underwater. The proteins involved in adhesion of mussels contain peptidyl-3-4-dihydroxy-phenylalanine (DOPA), a constituent not found in barnacle cement proteins. The reactive, oxidized form of DOPA, quinone, is thought to provide the moisture-resistance characteristic of mussel underwater adhesion. See, Yu M, Hwang, J, Deming, T J, Role of L-3,4-Dihydroxyphenylalanine in Mussel Adhesive Proteins, *Journal of the American Chemical Society*, 121: 5825–5826 (1999). DOPA can complex with metal ions and oxides and semimetals such as silicone, thus explaining the ability to adhere to rocks and glass. Other constituents of mussel adhesive proteins include lysine and glycine. Lysine may contribute to adhesion via ionic bonding to negatively charged surfaces like collagen and acidic polysaccharides. Proposed mechanisms for the strength and waterproof properties of the adhesive formed relate to recurring amino acid motifs (decapeptide repeats of 75–80 times in Mefp-1) and the hydroxylated amino acids found in the adhesive proteins. Polyphenolic proteins are non-toxic, biodegradable and have a low immunogenicity.

Mefp-1 is a polyphenolic protein with primarily structural properties. It is oxidized and cross-linked through the action of a catechol oxidase to form a hardened sheath (the byssal thread) that extends between the foot organ of the animal and the surface of attachment. The inner core of this structure is comprised of four collagens (with variants) with distinctive domains not found in other biological systems. This combination of proteins functions much like a natural epoxy adhesive. The cysteine-rich Mefp-2 forms the foam-like plaque component of the byssus. Mefp-4 and Mefp-5 are additional proteins located in the plaque. A hydroxyarginine-containing protein, Mefp-3, is believed to serve as a primer-like protein for this byssal plaque. See FIG. 1.

Byssal Thread Polyphenolic Protein: Mefp-1.

Mefp-1 was the first polyphenolic protein to be identified in the mussel byssus (See Waite J H, Tanzer M L, Polyphenolic Substance of *Mytilus edulis* Novel Adhesive Containing L-Dopa and Hydroxyproline, *Science*, 212 (4498): 1038–1040 (1981). The primary location of Mefp-1 is in the byssal threads, cross-linked via a polyphenol oxidase to form a sclerotonized sheath around the flexible, collagen inner-core. Byssal plaques contain approximately 5% of Mefp-1 as well. Mefp-1 adhesive properties are comparable to synthetic cyanoacrylate and epoxy resins.

Mefp-1 is a large, basic protein with very little secondary structure and a molecular mass of 130 kDa. Decapeptide and hexapeptide repeats containing numerous post-translational modifications (~60–70% of the amino acid residues are hydroxylated) provided the first indication of an adhesive-related protein unlike any others identified in nature. The hexapeptide repeat is AKPTYK. (SEQ ID NO. 21) The major decapeptide consensus repeat, consisting of AKPSY PPTYK (SEQ ID NO. 22) (where Y represents 3,4-dihydroxyphenyl-alanine (DOPA), P represents trans-2,3-cis-3,4-dihydroxyproline, and P̄ represents trans-4-hydroxy-L-proline) occurs approximately eighty times in Mefp-1. DOPA residues constitute 10–15% of the protein (See Waite J H, Evidence for a Repeating 3,4-Dihydroxyphenylalanine-Containing and Hydroxyproline-Containing Decapeptide in the Adhesive Protein of the Mussel, *Mytilus edulis*, Journal of Biological Chemistry, 258 (5): 2911–2915 (1983). The open conformation of the protein is believed to allow functional groups full accessibility for interactions with other proteins and a variety of surfaces, including glass, polytetrafluoroetheylene, and metals.

Mefp-1 has been previously commercialized as a source for mussel adhesive protein. Companies supplying Mefp-1 have obtained the pure protein from the byssal structures using protein extraction techniques (e.g. Sigma-Aldrich; BD Biosciences Clontech, formerly marketed by BioPolymers Corp of Farmington, Conn., under the trademark CELL-TAK) and recombinant protein techniques using synthetic gene constructs. However, currently there are no commercial sources for Mefp-1, due to the high cost of extraction methods and inconsistencies in quality of protein from recombinant protein techniques. All of the laboratory-prepared products were not as strong as the natural protein.

Mefp-1 requires oxidization by catechol oxidase or tyrosinase enzymes (or periodontate) in order to render the tyrosine residues converted to reactive DOPA residues required for strong adhesion. The enzyme oxidation may serve as an oxidative agent and as a copolymer. Molecular oxygen can also be used to oxidize DOPA to a quinone. Possible cross-linking agents are oxygen, polyvalent metal ions, $Fe^{3+}$ and $Al^{3+}$, aldehydes and many types of bi/poly-functional cross-linkers. The addition of other macromolecules to the Mefp-1 protein—such as collagen, casein or keratin—has been recommended by companies in order to increase the adhesive properties of the individual protein.

Mefp-1 in the form of CELL-TAK (BioPolymers Corp of Farmington, Conn.) has been tested as a surgical adhesive between a number of different cells or tissues from a range of species. For example, studies testing the efficiency of CELL-TAK (BioPolymers Corp of Farmington, Conn.) compared to other adhesives have included porcine cartilage, bone and skin (See Chivers R A, Wolowacz R G, The Strength of Adhesive-Bonded Tissue Joints, International Journal of Adhesion and Adhesives (1997), 17 (2): 127–132; rat tissue (See Schmidt S P, Resser J R, Sims R L, Mullins D L, Smith D J, The Combined Effects of Glycyl-L-Histidyl-L-Lysine-Copper (II) and CELL-TAK on the Healing of Linear Incision Wounds, Wounds A Compendium of Clinical Research and Practice, 6 (2): 62–67 (1994), rabbit corneas (See Robin J B, Picciano P, Kusleika R S, Salazar J, Benedict C, Preliminary Evaluation of the Use of Mussel Adhesive Protein in Experimental Epikeratoplasty, Archives of Ophthalmology, 106 (7): 973–977 (1988), and chicken osteoblasts and cartilage cells (See Fulkerson J P, Norton L A, Gronowicz G, Picciano P, Massicotte J M, Nissen C W, Attachment of Epiphyseal Cartilage Cells and 17/28 Rat Osterosarcoma Osteoblasts using Mussel Adhesive Protein, Journal of Orthopaedic Research, 8 (6): 793–798 (1990).

Studies have also included human breast cancer cells and mouse sperm cells. The best adhesion with CELL-TAK (BioPolymers Corp of Farmington, Conn.) has been shown to occur with cell cultures. Other testing of CELL-TAK (BioPolymers Corp of Farmington, Conn.) for industrial applications has included it's use as an enzyme immobilization matrix in the fabrication of enzyme-based electrodes (See Saby C, Luong J H T, *Mytilus edulis* Adhesive Protein (MAP) as an Enzyme Immobilization Matrix in the Fabrication of Enzyme-Based Electrodes, Electroanalysis, 10 (17): 1193–1199 (1998).

Purified polyphenolic protein was also shown to effectively immobilize human chorionic gonadotrophin to wells of a microtiter plate (See Burzio V A, Silva T, Pardo J, Burzio L O, Mussel Adhesive Enhances the Immobilization of Human Chorionic Gonadotrophin to a Solid Support, Analytical Biochemistry, 241 (2): 190–194 (1996). In addition, the immunoreactivity of the attached antigen used in the study was stable for several months. This example shows a possible tool for polyphenolic proteins in basic research and medical diagnostics.

Other *Mytilus* mussel species contain a protein analogous to Mefp-1, with differences in the decapeptide repeat frequency, residue composition, and non-repetitive regions.

Byssal Plaque Polyphenolic Proteins: Mefp-2, Mefp-3, Mefp-4 and Mefp-5

Mefp-2

Mefp-2 is found exclusively in byssal plaques, constituting from 25–40% of the total plaque proteins. Unlike Mefp-1, Mefp-2 is a smaller adhesive protein (molecular mass 42–47 kDa) with only 2–3 mol % DOPA and no hydroxylation of proline to trans-2,3-cis-3,4-dihydroxyproline or trans-4-hydroxy-L-proline. The DOPA residues occur primarily in the N- and C-terminal regions of the protein. Mefp-2 contains considerable secondary structure and is relatively resistant to a variety of proteases (compared to Mefp-1). The high cysteine content (6–7 mol %) coupled with tandemly repetitive motifs similar to epidermal growth factor, represents an adhesive protein with a stabilization role in the byssus (See Inoue K, Takeuchi Y, Miki D, Odo S, Mussel Adhesive Plaque Protein Gene is a Novel Member of Epidermal Growth Factor-like Gene Family, Journal of Biological Chemistry, 270 (12): 6698–6701 (1995).

An Mefp-2 multi-gene family may exist, based on evidence that at least three different repetitive motifs have been identified in the primary protein sequence (See Rzepecki L M, Hansen K M, Waite J H, Characterization of Cysteine-rich Polyphenolic Protein Family from the Blue Mussel, *Mytilus edulis*-L, Biological Bulletin, 183 (1): 123–137 (1992). A published full-length gene sequence for Mefp-2 is not available. However, investigation of Mefp-2 cDNA sequences of the invention supports the multi-gene family premise.

Mefp-3

Mefp-3 is the smallest byssal adhesive protein identified to date, with a molecular mass of ~5–7 kDa. See Papov V V, Diamond T V, Biemann K, Waite J H, Hydroxyarginine-Containing Polyphenolic Proteins in the Adhesive Plaques of the Marine Mussel, *Mytilus edulis*, Journal of Biological Chemistry, 270 (34): 20183–20192 (1995); Inoue K, Takeuchi Y, Miki D, Odo S, Harayama S, Waite J H, Cloning, Sequencing and Sites of Expression of Genes for the Hydroxyarginine-Containing Adhesive-Plaque Protein of the Mussel, *Mytilus galloprovincialis*, European Journal of Biochemistry, 239 (1): 172–176 (1996); Warner S C, Waite J H, Expression of Multiple Forms of an Adhesive Plaque Protein in an Individual Mussel, *Mytilus edulis*, Marine Biology, 134 (4): 729–734 (1999). Mefp-3 contains no repeats, 20–25 mol % DOPA, and a prevalence of 4-hydroxyarginine and tryptophan residues. Warner S C, Waite J H, "Expression of Multiple Forms of an Adhesive Plaque Protein in an Individual Mussel, *Mytilus edulis*", Marine Biology, 134 (4): 729–734 (1999); identified twenty gene variants (~0.3 kB) of Mefp-3 in the foot organ; however, only four or five proteins have actually been detected in plaques deposited on glass or plastic. The presence of a gene family for Mefp-3 supports the primer-like function of the protein in adhering to substrata. One hypothesis has been that deposition of a specific Mefp-3 variant is dependent upon the surface used for attachment. However, protein expression specific to substrate attachment has not been demonstrated to date.

Mefp-4

Mefp-4 is another protein identified in byssal plaques, with a molecular mass of 79 kDa (See, Vreeland V, Waite J H, Epstein L, "Polyphenols and Oxidases in Substratum Adhesion by Marine Algae and Mussels", Journal of Phycology, 34 (1): 1–8 (1998); Weaver, J K, "Isolation, Purification, and Partial Characterization of a Mussel Byssal Precursor Protein, *Mytilus edulis* foot protein 4", MS thesis, University of Delaware, Newark, (1998)) Mefp-4 contains elevated levels of glycine, arginine, and histidine, as well as 4 mol % DOPA. A unique tyrosine-rich octapeptide is present, with variations in residue substitutions giving rise to a family of proteins. This very large protein most likely serves a stabilization role in byssal plaques, as does Mefp-2. The sequence of the Mefp-4 gene has not been identified, nor are any analogs/homologs from other mussel species available to date.

Mefp-5

Mefp-5 is the most recent identified adhesive-related byssal plaque protein. See, Waite J H, Qin X X, "Polyphosphoprotein from the Adhesive Pads of *Mytilus edulis*", Biochemistry, 40 (9): 2887–2893 (2001). Mefp-5 is a relatively small protein with a molecular mass of 9.5 kDa, a 27 mol % DOPA content, and the presence of phosphoserine. Phosphoserine is known to occur in acidic mineral-binding motifs of proteins that bind calcareous materials (e.g., osteopontin); therefore, its presence in byssal plaques may aid in adhesion of one animal to a neighboring mussel's shell. Mefp-5 was formerly associated with the Mefp-3 family of variants, and similarly, plays an interfacial role as a primer for substrate adhesion. See also, M J Sever, et al., Metal-mediated cross-linking in the generation of a marin-mussel adhesive. Angewandte Chemie 43(4), 448–450.

An underwater adhesive will be a valuable asset to the military and industries such as forest products (composite wood products), building/construction, plastics, electronics, automotive, aviation, and the biomedical fields (dentistry, surgery, orthopedics, ophthalmology). All can benefit from an environmentally safe, strong, inexpensive alternative to the conventional adhesives available today. There are no conventional glues that can be applied in an aqueous environment and are impervious to water and turbulent forces. The development of a biomimetic glue product (an adhesive that employs man-made materials to mimic the efficient attachment mechanisms of the natural mussel) will revolutionize the field of adhesive technology. Mussel adhesive proteins represent a tantalizing target in the field of biomimetics. The challenge of resisting the effects of water: (i) its ability through hydrogen bonding to interfere with initial bonding between the substrate and adhesive; (ii) the attack by water on the adhesive-substrate interface through wicking and crazing; (iii) swelling of adhesive (and failure of the bond junction) through water absorption; and (iv) dissolution or erosion of the adhesive, have been met by the mussel byssus and the protein constituents secreted during its synthesis. For more than 20 years, researchers have studied mussel adhesion to gain clues to design better glues for wet environments, such as in dentistry, as a surgical glue and in industry. Two commercial products for attachment of cells to plastic vessels in cell culture applications have been introduced (CELL-TAK® (BioPolymers Corp of Farmington, Conn.) and AdheraCell/Genex Corp.), and several U.S. patents cover aspects of the repeating decapeptide motif, isolation of polyphenolic proteins from mussels and recombinant forms of Mefp-1.

Genetic Approaches

Reverse-genetics approaches to obtaining complete gene sequences, enzymatic screening of a cDNA library from the foot organ of *M. edulis*, and the use of DNA probes allow for detection of transcripts actively expressed and transcribed by the mussel. With the complete gene sequences, an alternate host system can be employed to produce the adhesive proteins of interest for future analyses from protein chemistry, novel microscopy, and adhesive science disciplines. The adhesives industry will require a large quantity of protein to perform adequate testing and analyses for future adhesive technologies.

In the first reverse-genetics strategy, an approach is taken to identify known genes encoding adhesive proteins of interest. For this method, PCR (polymerase chain reaction) primers are designed for the genes of interest based on available nucleotide and amino acid sequences from *M. edulis* and other mussel species. The primers are combined with total RNA isolated from the foot organ of *M. edulis* in an RT-PCR (reverse transcription followed by PCR) reaction to yield a product corresponding to the gene of interest. This cDNA (c="complementary") product is then inserted (cloned) into a plasmid vector (currently obtained from a vendor). The clone for the adhesive gene of interest is now packaged for analysis by DNA sequencing and for insertion (transformation) into a suitable host for recombinant protein expression. DNA sequencing of the clone is critical in 1) determining that the clone is full-length e.g. contains the start and stop signal for translation of the full gene to protein, and 2) identifying variants in any of the gene sequences.

In the second reverse-genetics approach, a cDNA library is constructed from RNA isolated from the foot organ of *M. edulis*. This library consists of individual clones in wells of a microtiter plate. High-throughput DNA sequencing of the microtiter plates containing the clones, followed by analysis using available bioinformatics software programs, will enable 1) a determination of all of the genes presently expressed in the foot of the mussel, and 2) a determination of known and possibly novel adhesive proteins expressed in the foot of the mussel. The treatment of mussels prior to excision of their foot organ for RNA isolation (e.g. exposure to various surfaces, water conditions) may play a role in the expression of genes in the foot organ.

An enzymatic assay is a third strategy to obtain the polyphenoloxidase (catechol oxidase) gene. In this assay, microtiter plates containing either 1) all clones from a foot organ cDNA library or 2) only clones identified by DNA sequencing to resemble a polyphenoloxidase enzyme, are subjected to addition of an appropriate substrate for colorimetric indication of active enzyme activity. It is important that the active form of the protein be determined for subsequent adhesive formulation determinations.

A fourth strategy to obtain genes for adhesive proteins, involves the development of nucleotide probes based on known DNA sequences or protein sequence motifs in the respective genes. These probes are then tested against a cDNA foot library from *M. edulis*.

PREFERRED EMBODIMENTS

The present invention relates to the adhesive protein, Mepf-1, and the nucleotide sequences encoding such protein, found in the blue mussel, *Mytilus edulis*. (Sequence ID NO: 1) and (SEQ ID NO: 16) describe the DNA sequences encoding Mefp-1 (full and partial sequences, respectively). (SEQ ID NO: 2) and (SEQ ID NO: 20) illustrate the corresponding amino acid sequences for the above-mentioned nucleotide sequences.

Nucleotide Sequences

The scope of the present invention is not limited to the exact sequence of the nucleotide sequences set forth in (SEQ ID NO: 1) or the use thereof. The invention contemplates certain modifications to the sequence, including deletions, insertions, and substitutions, that are well known to those skilled in the art. For example, the invention contemplates modifications to the sequence found in (SEQ ID NO: 1) with codons that encode amino acids that are chemically equivalent to the amino acids in the native protein. An amino acid substitution involving the substitution of an amino acid with a chemically equivalent amino acid is known as a conserved amino acid substitution.

Chemical equivalency can be determined by one or more the following characteristics: charge, size, hydrophobicity/hydrophilicity, cyclic/non-cyclic, aromatic/non-aromatic etc. For example, a codon encoding a neutral non-polar amino acid can be substituted with another codon that encodes a neutral non-polar amino acid, with a reasonable expectation of producing a biologically equivalent protein.

Amino acids can generally be classified into four groups. Acidic residues are hydrophillic and have a negative charge to loss of H+ at physiological pH. Basic residues are also hydrophillic but have a positive charge to association with H+ at physiological pH. Neutral nonpolar residues are hydrophobic and are not charged at physiological pH. Neutral polar residues are hydrophillic and are not charged at physiological pH. Amino acid residues can be further classified as cyclic or noncyclic and aromatic or nonaromatic, self-explanatory classifications with respect to side chain substituent groups of the residues, and as small or large. The residue is considered small if it contains a total of 4 carbon atoms or less, inclusive of the carboxyl carbon. Small residues are always non-aromatic.

Of naturally occurring amino acids, aspartic acid and glutamic acid are acidic; arginine and lysine are basic and noncylclic; histidine is basic and cyclic; glycine, serine and cysteine are neutral, polar and small; alanine is neutral, nonpolar and small; threonine, asparagine and glutamine are neutral, polar, large and nonaromatic; tyrosine is neutral, polar, large and aromatic; valine, isoleucine, leucine and methionine are neutral, nonpolar, large and nonaromatic; and phenylalanine and tryptophan are neutral, nonpolar, large and aromatic. Proline, although technically neutral, nonpolar, large, cyclic and nonaromatic is a special case due to its known effects on secondary conformation of peptide chains, and is not, therefore included in this defined group.

There are also common amino acids which are not encoded by the genetic code include by example and not limitation: sarcosine, beta-alanine, 2,3-diamino propionic and alpha-aminisobutryric acid which are neutral, nonpolar and small; t-butylalanine, t-butylglycine, methylisoleucine, norleucine and cyclohexylalanine which are neutral, nonpolar, large and nonaromatic; ornithine which is basic and non-cylclic; cysteic acid which is acidic; citrulline, acetyl lysine and methionine sulfoxide which are neutral, polar, large and nonaromatic; and phenylglycine, 2-naphtylalanine, β-2-thienylalanine and 1,2,3,4-tetrahydroisoquinoline-3-carboxylic acid which are neutral, nonpolar, large and aromatic. Other modifications are known in the art some of which are discussed in U.S. Pat. No. 6,465,237 issued to Tomlinson on Oct. 15, 2002.

Cloning and Sequencing of Mepf-1: SEQ ID NO: 1 and 16

For SEQ ID NO: 16 (clone designation LIVE7): Total RNA from the foot organ of *M. edulis* was supplied to the customer by Invitrogen Corporation (Carlsbad, Calif.). Invitrogen's cDNA library was constructed using the following strategy. First strand cDNA was synthesized using AMV Reverse Transcriptase with a Not T primer. The Not I primer is a 39 base pair primer which consists of 18 T residues and a Not I restriction site. The RNA-cDNA hybrid created by first strand synthesis was converted to double stranded cDNA by DNA Polymerase I in combination with RNase H and *E. coli* DNA ligase. After addition of BstX I adapters, the cDNA was digested with Not I and sized on an agarose gel. Size selected cDNA (>500 bp) was ligated into BstX I/Not I digested phagemid vector pYES2 and transformed into the *E. coli* strain TOP10F'. pYES2 is a yeast expression vector. Library amplification was performed by plating over 20 large plates and incubating overnight at 37° C. The cells were scraped from the plates, resuspended into SOC media/20% glycerol and aliquoted into 6 tubes with each vial containing approximately 2 mL. Vials were stored at −80° C. until use. Validation: number of primary recombinants=4.35×10$^6$ ratio containing inserts=10/10, average insert size of the clones analyzed=1.22 kB. The original cDNA library from Invitrogen was designated as #1 (I). Subsequent replications and platings were designated as cDNA libraries #2 (II) and #3 (III).

Table 1. Primers for RT-PCR: Mefp-1 (SEQ ID NO: 1)

| Primer | F/R | Target | DNA Sequence: 5' to 3' | Restriction nt Site | Amino Acids |
|---|---|---|---|---|---|
| 516 | F | Mefp-1 | gagctcgcatcatggagggaatc (SEQ ID: 3) | 23 Sac I | . . . MEGI (SEQ ID: 14) |
| 517 | R | Mefp-1 | gcggccgccacttaatattgtgatggatagc (SEQ ID: 4) | 31 Not I | . . . YPSQY* (SEQ ID: 15) |

For SEQ ID NO: 1, specific primers were designed (as shown in Table 1) based upon GenBank Accession No. D63778, *Mytilus galloprovincialis* (SEQ ID NO: 13) mRNA adhesive plaque protein. Primer set 516 (SEQ ID NO: 3)/517(SEQ ID NO: 4) produced clone #21 (SEQ ID NO: 1) The *M. galloprovincialis* sequence was used because (1) the *M. edulis* published genomic clone is missing the 5' start and (2) the Mefp-2 sequences that the inventors had also identified appeared to be identical in codon usage with the published Mgpf-2 sequence. It was later realized that the 3' end of the genomic clone varies from Mgfp-1; therefore the Mefp-1 clone #21 (SEQ ID NO: 1) differs at the 3' end due to the reverse primer design of primer #517. The relationship between the primers and the GenBank sequence are shown below:

```
516        1                                23
     5'  gagctc  gcatc            atg gag gga atc 3'    (SEQ ID NO: 3)
            SacI                   M   E   G   I        (SEQ ID NO: 14)
Mgfp1                             8                19
                                  atg gag gga atc       (SEQ ID NO: 17)
517        31                                        1
     3'-5'    cg ata ggt agt gtt ata att cac  cgccggcg  (SEQ ID NO: 4)
     5'-3'    gc tat cca tca caa tat taa gtg  gcggccgc  (SEQ ID NO: 19)
               Y   P   S   Q   Y   *            Not I  (SEQ ID No: 15)
Mgfp1       2244                         2266
            gc tat cca tca caa tat taa gtg  aagacaag    (SEQ ID NO: 18)
```

The nucleotide sequence for Mepf-1 clone #21 (SEQ ID NO: 1) was amplified by RT-PCR using the designed primers with total RNA isolated from the foot organ of *M. edulis*. Following first strand cDNA synthesis, PCR was carried out as described below. 1 µL cDNA, 5 µL 10× Buffer for AccuTaq LA DNA Polymerase (Sigma; St. Louis Mo.), 1 µL DMSO (Boehringer; Mannheim; Germany), 1 µL dNTPs (at 10 mM each), 2 µL primer set 516/517 (for Mefp-1; at 100 pmol/µL), 40 µL sterile water and 0.5 µL AccuTaq LA DNA Polymerase were added to a thin-walled 0.5 mL PCR tube. Amplification was performed on a Hybaid PCR Express thermocycler (Hybaid; UK) under the following conditions: 94° C.—3 minutes; 35 cycles of: 94° C.—45 seconds, 61° C.—1:30 minutes, 68° C.—3:00 minutes; 68° C.—10:00 minutes; final hold at 4° C. The PCR reaction was analyzed on a 1% agarose gel.

Cloning was performed per the pYES2.1 TOPO TA Cloning Kit (Invitrogen; Carlsbad, Calif.). Transformants were picked and screened by restriction enzyme digestion (SacI and NotI double restriction digest, per New England BioLabs; Beverly, Mass.) and DNA sequencing. Clone designation #21 (SEQ ID NO: 1) was determined to be a complete cDNA clone for Mefp-1.

DNA sequencing of all potential Mefp-1 clones was performed with a LiCor 4000L DNA Sequencer (LiCor Inc.; Lincoln, Nebr.) and with an ABI 3700 DNA Sequencer using BigDye v2.0, v3.0 and v3.1 chemistries (Applied Biosystems; Foster City, Calif.). Oligonucleotide sequencing primers were obtained from Invitrogen cloning kits, an EpiCentre EZ::TN Plasmid-Based Deletion Machine kit (Epicentre; Madison, Wis.), LiCor, Operon Technologies, Inc. (Alameda, Calif.), and MWG Biotech (UK). Primers used with the LiCor sequencer were IRD 800 dye-labeled. Primers used with the Applied Biosystems sequencer were unlabeled. See Table 2 for details of DNA sequencing primers used.

Screening of the cDNA libraries was performed following 96-well plasmid preparation methods from various vendors (e.g. Qiagen (Alameda, Calif.) and Promega (Madison, Wis.)).

The EZ::TN Plasmid-Based Deletion Machine protocol was used to produce deletion clones of Mefp-1 clone #21 (SEQ ID NO: 1) to aid in obtaining the full DNA sequence.

Sequencing primers designed for vector targets were designed based upon vector sequences provided by Invitrogen or EpiCentre. Primers designed by the inventors for targeting DNA sequence of Mefp-1 were based upon clone #21 consensus sequence.

Sequencing primers for vector targets were obtained from Invitrogen or EpiCentre. Primers designed by inventors (labeled HS/FFR) for targeting the DNA sequence of Mefp-1 were based upon clone #21 consensus sequence (SEQ ID NO: 1).

TABLE 2

Sequencing Primers

| Primer | F/R | Target: | DNA Sequence: 5' to 3' | nt |
|---|---|---|---|---|
| T7 (Standard) Invitrogen Corporation | F | pYES2 and pYES2.1/ V5-His-TOPO | TAATACGACTCACTATAGGG (SEQ ID NO: 5) | 20 |
| V5C-term Reverse Invitrogen Corporation | R | pYES2.1/ V5-His-TOPO | ACCGAGGAGAGGGTTAGGGAT (SEQ ID NO: 6) | 21 |
| 506 by HS/FFR | R | pYES2 | TTTCGGTTAGAGCGGATG (SEQ ID NO: 7) | 18 |
| 507 by HS/FFR | R | pYES2 | AGGGCGTGAATGTAAGCGTG (SEQ ID NO: 8) | 20 |
| F#21Int859 by HS/FFR | F | Mefp-1 internal | GCAAAGCCAACTTATATAG (SEQ ID NO: 9) | 19 |
| R#21Int529 by HS/FFR | R | Mefp-1 internal | GAAGAGGGATAACTTGACTTGG (SEQ ID NO: 10) | 22 |
| FP-1 EpiCentre | F | pPDM-1 | CCCAATACGCAAACCGCCTCT (SEQ ID NO: 11) | 21 |
| RP-1 EpiCentre | R | pPDM-1 | TTAGAAAAATAAACAAATAGGGGTT (SEQ ID NO: 12) | 25 |

Expression of Mefp-1 Protein

Expression of recombinant Mefp-1 protein from clone #21 (SEQ ID NO: 1) is performed by following the protocol set forth by Invitrogen. Expression is performed with the pYES2 system in the yeast strain *Saccharomyces cerevisiae*.

A 30-liter fermentor (Bio Flo 4500—New Brunswick Scientific; Edison, N.J.) is used to scale-up from the Invitrogen protocol.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefore, is not intended to limit the claimed processes to any order except as may be specified in the claims. Accordingly, the invention is limited only by the following claims and equivalents thereto.

All publications and patent documents cited in this application are incorporated by reference in their entirety for all purposes to the same extent as if each individual publication or patent document were so individually denoted.

The invention claimed is:

1. An isolated nucleic acid sequence encoding an adhesive protein derived from a mollusk, comprising a nucleotide sequence encoding a polypeptide having 90% identity to SEQ ID NO:2.

2. The isolated nucleic acid sequence of claim 1, wherein the nucleotide sequence encodes the polypeptide of SEQ ID NO:2.

3. An isolated nucleic acid sequence encoding an adhesive protein derived from a mollusk, comprising a nucleotide sequence encoding a polypeptide having 98% identity to SEQ ID NO:20.

4. The isolated nucleic acid sequence of claim 3, wherein the polypeptide sequence comprises SEQ ID NO:20.

5. The isolated nucleic acid sequence of claim 1, wherein the nucleotide sequence comprises the nucleotide sequence of SEQ ID NO:1 or a degenerate variant of SEQ ID NO:1.

6. The isolated nucleic acid sequence of claim 1, wherein the nucleotide sequence consists of SEQ ID NO:1.

7. The isolated nucleic acid sequence of claim 1, wherein the nucleotide sequence comprises at least 500 contiguous nucleotides of SEQ ID NO:1.

8. The isolated nucleic acid sequence of claim 1, wherein the nucleotide sequence has at least 98% identity to SEQ ID NO:1.

9. The isolated nucleic acid sequence of claim 1, wherein the nucleotide sequence encodes a polypeptide having the sequence of SEQ ID NO:2 with a conservative amino acid substitution.

10. The isolated nucleic acid sequence of claim 3, wherein the nucleotide sequence comprises the nucleotide sequence of SEQ ID NO:16 or a degenerate variant of SEQ NO:16.

11. The isolated nucleic acid sequence of claim 3, wherein the nucleotide sequence consists of SEQ ID NO:16.

12. The isolated nucleic acid sequence of claim 3, wherein the nucleotide sequence encodes a polypeptide having the sequence of SEQ ID NO:20 with a conservative amino acid substitution.

13. An expression vector comprising the nucleotide sequence of claim 3, operably linked to an expression control sequence.

14. An expression vector comprising the nucleotide sequence of claim 1, operably linked to an expression control sequence.

* * * * *